(12) United States Patent
Manning et al.

(10) Patent No.: US 9,770,401 B2
(45) Date of Patent: *Sep. 26, 2017

(54) SKIN TIGHTENING COMPOSITIONS

(71) Applicant: L'OREAL, Paris (FR)

(72) Inventors: Lauren E. Manning, Hoboken, NJ (US); Miao Wang, Westfield, NJ (US); Angelike A. Galdi, Westfield, NJ (US); Catherine Chiou, Saddle Brook, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/985,616

(22) Filed: Dec. 31, 2015

(65) Prior Publication Data

US 2017/0189299 A1 Jul. 6, 2017

(51) Int. Cl.
| | | |
|---|---|---|
| *A61K 8/73* | (2006.01) | |
| *A61K 8/81* | (2006.01) | |
| *A61K 8/25* | (2006.01) | |
| *A61K 8/26* | (2006.01) | |
| *A61Q 19/00* | (2006.01) | |
| *A61Q 19/08* | (2006.01) | |

(52) U.S. Cl.
CPC ............... *A61K 8/73* (2013.01); *A61K 8/25* (2013.01); *A61K 8/26* (2013.01); *A61K 8/8164* (2013.01); *A61Q 19/00* (2013.01); *A61Q 19/007* (2013.01); *A61Q 19/08* (2013.01); *A61K 2800/48* (2013.01); *A61K 2800/548* (2013.01); *A61K 2800/594* (2013.01)

(58) Field of Classification Search
None
See application file for complete search history.

(56) References Cited

U.S. PATENT DOCUMENTS

| 4,664,910 A | * | 5/1987 | Caserio ............... A61K 8/63 |
| | | | 424/70.8 |
| 2003/0082221 A1 | | 5/2003 | O'Halloran et al. |
| 2011/0300196 A1 | * | 12/2011 | Mohammadi ........ A45D 44/002 |
| | | | 424/401 |
| 2013/0189332 A1 | * | 7/2013 | Breyfogle ............... A61K 8/25 |
| | | | 424/401 |
| 2015/0373380 A1 | | 12/2015 | Tsukagoshi |

FOREIGN PATENT DOCUMENTS

| EP | 2221045 A1 * | 8/2010 | ........... A61K 8/8147 |
| EP | 2404642 A2 | 1/2012 | |
| WO | WO 2013078550 A1 * | 6/2013 | ........... A61K 31/732 |

OTHER PUBLICATIONS

Notification of Transmittal of the International Search Report and the Written Opinion of the International Searching Authority, or the Declaration, as well as the Search Report and Written Opinion, received in PCT/US16/68213, mailed Mar. 16, 2017.

* cited by examiner

*Primary Examiner* — Tracy Vivlemore
*Assistant Examiner* — Monica Shin
(74) *Attorney, Agent, or Firm* — Polsinelli PC

(57) ABSTRACT

The present disclosure relates to cosmetic compositions that provide immediate skin-tightening and long-lasting improvements to the skin for the treatment of, for example, eye bags, facial wrinkles, and other age-related skin imperfections. The compositions comprise: (a) at least one film former; (b) at least one polyvalent silicate thickener; (c) at least one anionic associative polymeric thickener; (d) at least one plasticizer; and (e) optionally, at least one cosmetic powder.

3 Claims, 2 Drawing Sheets

SKIN TIGHTENING COMPOSITIONS

FIELD OF THE DISCLOSURE

The present disclosure relates to cosmetic compositions that provide immediate and long-lasting improvement to the skin. In particular, the compositions provide a physical tightening effect to the skin and are therefore useful for treating eye bags, facial wrinkles, and other age-related skin imperfections.

BACKGROUND OF THE DISCLOSURE

Skin produces less collagen and elastin as it ages. For example, after the age of twenty, a person (human) produces about 1 percent less collagen in the skin each year. As a result, the skin becomes thinner and more fragile. Inevitably, wrinkles, crow's feet, age-spots, eye bags, and the like, begin to form.

Consumers often wish to improve the appearance of such age-related skin imperfections, preferably with instantaneous results. Many consumer products and procedures devoted to hiding and reducing wrinkles are available. Some products and procedures are simple and inexpensive, for example, applying make-up, particularly a primer or colored foundation, to cover the skin (and thereby cover and/or fill the wrinkles and provide a smoother look). Far more expensive and drastic procedures, such as surgical face lifts and Botox® injections, are also used to reduce the appearance of wrinkles. However, many consumers either cannot afford, or do not wish, to undergo such drastic cosmetic procedures. There are a number of lotions and creams which are formulated to hydrate the skin and make it more supple, thereby reducing the appearance of wrinkles. Some of these products contain active ingredients, for example, niacinamide, that help repair and rejuvenate skin over time. Unfortunately, however, all of these products and procedures have drawbacks.

Make-up products are often visible, offer minimal texture benefits, and have no long-term lasting effect on the skin. After removal of the make-up, the skin looks the same as before the make-up was applied. Common skin care products can have chronic, acute or both effects on the skin. Hydration and optical effects are common acute benefits, but these benefits quickly wear-off over time.

Attempts have been made to develop new categories of products to improve the appearance of skin without the drawbacks of existing products and procedures. One such family of products can be generally classified as "adhesive, contractile film formers". Film formers are chemical compositions that when applied to skin, leave a pliable, cohesive and continuous covering. A select group of film formers are also adhesive to the skin and contractile.

Sodium silicate has been found to have dramatic, instant results. See patent applications US2015/00373380, US2013/0189332, EP2404642. The compositions in these patent applications, however, quickly lose their skin tightening effect. For example, the films lose their elasticity and quickly begin to whiten, crack, and peel. The instant disclosure is directed to new and improved long-lasting skin tightening compositions that do not suffer the drawbacks of other skin-tightening compositions.

BRIEF SUMMARY OF THE DISCLOSURE

The current disclosure relates to a skin tightening composition that imparts an instant sensation and physical skin tightening effect upon application to the skin, in particular, to eye bags and eye or facial wrinkles, without the drawbacks of other products. The present disclosure relates to a skin tightening film forming composition, which is typically an aqueous composition, comprising:
(a) at least one film former;
(b) at least one polyvalent silicate thickener;
(c) at least one anionic associative polymeric thickener;
(d) at least one plasticizer; and
(e) optionally, at least one cosmetic powder.

The composition typically provides an immediate tightening of the skin and smoothes imperfections of the skin upon application.

The composition may have an alkaline pH, for example, it may have a pH value from about to 10 to about 12. Furthermore, the composition may be in the form of a liquid dispersion, a gel, a cream, a lotion, a mousse, or a spray. Likewise, the composition may be in the form of a liquid emulsion, such as a liquid-lotion, liquid-gel, liquid-cream, or a cream emulsion, such as a thick cream or gel-cream, foam or mousse wherein the liquid emulsion form has a thinner consistency than the cream emulsion form.

The instant disclosure also relates to methods for improving the appearance of skin comprising applying the compositions described herein to the skin. For example, the instant disclosure relates to methods for firming and/or tightening the skin comprising applying the compositions described herein to the skin and forming a skin-tightening film or layer on the skin. In some instances, the compositions are applied to the skin of the face, and/or more specifically around the eyes, around the mouth, and/or around the neck of a human face. The methods of improving the appearance of skin include methods for treating or reducing the appearance of wrinkles, blemishes, dryness, roughness, dullness, age spots, sagging, and/or puffy skin.

The compositions of the present disclosure are surprisingly stable, elastic, and provide an unexpectedly long-lasting skin tightening effect to the skin. Unlike other products, the films formed on the skin with the instant compositions do not dry-out and whiten, crack, or peel. Instead, they remain flexible (elastic), durable, and comfortable. Moreover, the compositions (and resulting films) hydrate and protect the underlying skin.

DESCRIPTIONS OF THE DRAWINGS

Implementation of the present technology will now be described, by way of example only, with reference to the attached figures, wherein.

Figure 1:
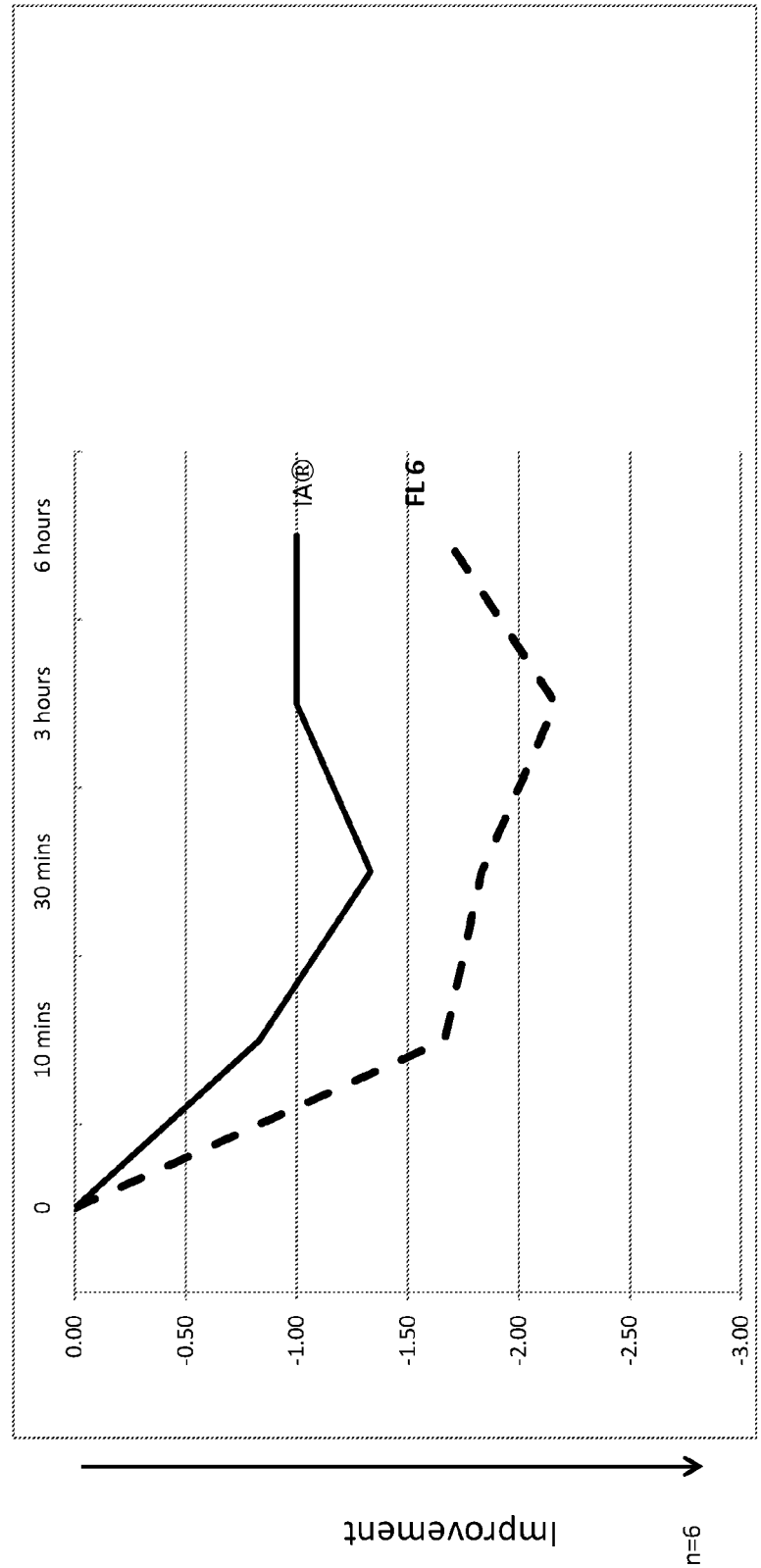
FIG. 1 is a graph comparing the results of inventive Formula 6 and the commercially available product Instant Ageless® on under eye bags. The graph illustrates time versus improvement of the under eye bags.

It should be understood that the various aspects provided by the figures are not limited to the arrangements and instrumentality shown in the figures.

DETAILED DESCRIPTION OF THE DISCLOSURE

As mentioned previously, the present disclosure relates to cosmetic compositions that provide instantaneous and long-lasting improvement to the skin. In particular, the compositions provide a tightening effect on skin and are therefore useful for treating eye bags, facial wrinkles, and other age-related skin imperfections. Typically, the compositions of the instant disclosure comprise: (a) at least one film former; (b) at least one polyvalent silicate thickener; (c) at least one anionic associative polymeric thickener; (d) at least one plasticizer; and (e) optionally, at least one cosmetic powder. For example, the composition s may comprise:
- (a) from about 1% to about 20% by weight of at least one film former;
- (b) from about 0.3% to about 0.7% by weight of at least one polyvalent silicate thickener;
- (c) from about 0.5% to about 15% by weight of at least one anionic associative polymeric thickener;
- (d) from about 2% to about 15% by weight of at least one plasticizer; and
- (e) optionally, from about 0.1% to about 10% by weight of at least one cosmetic powder.

Upon application to the skin, the compositions provide an immediate tightening sensation and reduce skin imperfections.

The compositions can have an alkaline pH. For example, in some cases, the pH value may be in the range of 10 to 12, 10.5 to 11.5, or 11 to 11.5.

The at least one film former may be, for example, sodium silicate, colloidal silica, pullulan, polycacrylate-21 (and) acrylates/dimethylaminoethylmethacrylate copolymer, polyurethanes, polysaccharides, polyvinylpyrrolidone, polyacrylates, acrylate copolymers, and the mixtures thereof. In some cases, the at least one film former comprises a polysaccharide, which may have one or more free hydroxyl groups. Furthermore, in some cases, the polysaccharide is pullulan. In some cases, the composition comprises at least two film formers, which may be any two film formers, e.g., sodium silicate and pullulan. Typically, the at least one film former is present in an amount from 1% to 20%, 1% to 18%, 1% to 16%, 1% to 14%, 1% to 12%, 1% to 10%, 1% to 8%, 2% to 20%, 2%, 18%, 2% to 16%, 2% to 16%, 2% to 14%, 2% to 12%, 2% to 10%, 2% to 8%, 3% to 20%, 3% to 18%, 3% to 16%, 3% to 14%, 3% to 12%, 3% to 10%, 3% to 8%, 4% to 20%, 4% to 18%, 4% to 16%, 4% to 14%, 4% to 14%, 4% to 12%, 4% to 10%, 4% to 8%, 5% to 20%, 5% to 18%, 5% to 16%, 5% to 14%, 5% to 12%, 5% to 10%, 5% to 8%, or 3% to 15%, by weight of the total weight of the composition.

The polyvalent silicate thickener may be selected from the group consisting of magnesium silicate, calcium silicate, aluminum silicate, a polyvalent silicate clay, montmorillonite, bentonite, smectite, and mixtures thereof. In some cases, the polyvalent silicate thickener is montmorillonite. In some cases, the polyvalent silicate thickener is organically modified clay such as kaolinite, smectite, bentonite, and/or montmorillonite The polyvalent silicate thickener is typically present in an amount of 0.1% to 0.9%, 0.1% to 0.8%, 0.1% to 0.7%, 0.2% to 0.9%, 0.2% to 0.8%, 0.2% to 0.7%, 0.3% to 0.9%, 0.3% to 0.8%, 0.3% to 0.7%, 0.4% to 0.9%%, 0.4% to 0.8%, 0.4% to 0.7%, 0.4% to 0.9%, 0.4% to 0.8%, 0.4% to 0.7%, 0.4% to 0.6%, or about 0.5%.

The compositions of the disclosure typically include at least one anionic associative polymeric thickener. The at least one anionic associative polymeric thickener may be selected from the group consisting of an acrylate copolymer, an acrylates/beheneth-25 methacrylate copolymer, an acrylates/steareth-20 methacrylate copolymer, and mixtures thereof. Furthermore, the at least one anionic associative polymeric thickener may include acrylates/steareth-20 methacrylate copolymer such as Aculyn™ 22 (Dow Chemical Company); acrylates/beneneth-25 methacrylate copolymer such as Novethix™ (Lubrizol); acrylate copolymer such as Carbopol® Aqua SF-1 Polymer (Lubrizol). The at least one anionic associative polymer thickener is typically present in an amount from 0.5% to 15%, 1% to 15%, 1% to 14%, 1% to 13%, 1% to 12%, 1% to 10%, 1% to 8%, 2% to 15%, 2% to 14%, 2% to 13%, 2% to 12%, 2% to 10%, 2% to 8%, or 2% to 6%, by weight of the total composition. Many anionic associative polymeric thickeners are water-soluble, and increase the viscosity of water or form an aqueous gel when the cosmetic compositions of the disclosure are dispersed/dissolved in water.

The compositions of the disclosure typically include at least one plasticizer. The at least one plasticizer may be, for example, propylene glycol, polyethylene glycol, glycerol, sorbitol, dipropylene glycol, glycerin, propane diol, triethyl citrate, isohexadecane, and sodium hyaluronate. Typically, the plasticizer is present in an amount of 1% to 15%, 1% to 14%, 1% to 13%, 1% to 12%, 1% to 11%, 1% to 10%, 2% to 15%, 2% to 14%, 2% to 13%, 2% to 12%, 2% to 11%, 2% to 10%, 5% to 15%, 5% to 14%, 5% to 13%, 5% to 12%, 5% to 11%, 5% to 10%, or 9% to 11% by weight of the total weight of the composition.

The compositions described herein may include at least one cosmetic powder. Cosmetic powders can be used to help formulate compositions that are smooth and soft on the skin. Representative cosmetic powders include, but are not limited to, talc, mica, magnesium carbonate, calcium carbonate, magnesium silicate, aluminum magnesium silicate, silica, titanium dioxide, zinc oxide, red iron oxide, yellow iron oxide, black iron oxide, polyethylene powder, methacrylate powder, polystyrene powder, silk powder, crystalline cellulose, starch, titanated mica, iron oxide titanated mica, bismuth oxychloride, and the like. Additional powders include, but are not limited to, inorganic powders, such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder, such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder, such as hydroxyethyl cellulose and sodium carboxymethyl cellulose, ethylene glycol monostearate; inorganic white pigments, such as magnesium oxide. Representative cosmetic powders include, for example, polymethylsilsesquioxane, methyl polymethacrylate crosspolymer, Nylon-12, silica and boron nitride, and combinations thereof.

In some cases, the cosmetic powder may be selected from the group consisting of talc, mica, magnesium carbonate, calcium carbonate, magnesium silicate, aluminum magnesium silicate, silica, titanium dioxide, zinc oxide, red iron oxide, yellow iron oxide, black iron oxide, polyethylene powder, methacrylate powder, polymethyl Methacrylate, polystyrene powder, silk powder, crystalline cellulose, and mixtures thereof. In some cases, the cosmetic powder is polymethyl methalcrylate.

When present, the one or more cosmetic powders may be present in an amount of 0.1% to about 25%, 0.1% to 20%, 0.1% to 15%, 0.1% to 10%, 0.1% to 8%, 0.1% to 6%, 0.1% to 4%, 0.5% to 20%, 0.0.5% to 15%, 0.5% to 10%, 0.5% to 8%, 0.5% to 6%, 0.5% to 4%, 1% to 20%, 1% to 15%, 1% to 10%, 1% to 8%, 1% to 6%, 1% to 4%, 2 to 10%, 2% to 8%, 2% to 6%, or 3% to 7%, based on the total weight of the composition.

The instant disclosure also relates to methods for improving the appearance of skin comprising applying the compositions described herein to the skin. Furthermore, the instant disclosure relates to methods for firming and/or tightening the skin comprising applying the compositions described herein to the skin and forming a skin-tightening film or layer on the skin. In some instances, the compositions are applied to the skin of the face, and/or more specifically around the eyes, around the mouth, and/or around the neck. The methods of improving the appearance of skin include methods for treating or reducing the appearance of wrinkles, blemishes, dryness, roughness, dullness, age spots, and sagging, and/or puffy skin.

The compositions of the present disclosure may be in the form of a liquid dispersion, a gel, a cream, a lotion, a mousse, or a spray. The composition may be in the form of a liquid emulsion, such as a liquid-lotion, liquid-gel, liquid-cream, or a cream emulsion, such as a thick cream or gel-cream, foam or mousse wherein the liquid emulsion form has a thinner consistency than the cream emulsion form.

The compositions of the present disclosure are typically aqueous compositions. For example, the compositions may have 20% to 80%, 20% to 70%, 20% to 60%, 20% to 50%, 20% to 40%, 20% to 30%, 30% to 80%, 30% to 70%, 30% to 60%, 30% to 50%, 30% to 40%, 35% to 65%, or 40% to 60% water.

EXAMPLES

The following Examples are provided for illustrative purposes only, and are not intended to be limiting.

Example 1

Formulas 1-22

TABLE 1

| | Formula | | | | |
|---|---|---|---|---|---|
| Ingredient/US INCI Name | 1 % | 2 % | 3 % | 4 % | 5 % |
| Sodium Silicate | 3.5-5.0 | 5.5-5.8 | 6-6.8 | 7.5-8 | 8.5-9.5 |
| Polyvalent Silicate[1] | 0.50-0.70 | 0.6-0.7 | 0.3-0.5 | 0.4-0.6 | 0.6-0.7 |
| Acrylates Copolymer | 0.5-2.0 | 6-10 | 11-15 | 2-6 | 9-13 |
| Second Film Former[2] | 4.0-5.0 | 3.0-4.0 | 8-10 | 2-3 | 5-4 |
| Cosmetic Powder | 3.0 | 3.0 | 3.0 | 3.0 | 3.0 |
| Water | QS | QS | QS | QS | QS |
| Plasticizer[3] | 8-10 | 4.0-6.0 | 10-12 | 5-7 | 3-5 |

[1]Vermiculite, Montmorillonite.
[2]Polyurethanes, Polysaccharides, Polyvinylpyrrolidone, Acrylates and Colloidal Silicate.
[3]Propylene Glycol, Polyethylene Glycol, Glycerol, Sorbitol, Dipropylene Glycol, Glycerin, Propanediol, Triethyl Citrate, Isohexadecane.

TABLE 2

| | Formula | | | | | |
|---|---|---|---|---|---|---|
| Ingredient/US INCI Name | 6 % | 7 % | 8 % | 9 % | 10 % | 11 % |
| Sodium Silicate | 5 | 5.6 | 6.5 | 7.5 | 8 | 9 |
| Montmorillonite | 0.5 | 0.7 | 0.4 | 0.6 | 0.6 | 0.7 |
| Acrylates Copolymer | 3 | 7 | 13 | 4 | 12 | 11 |
| Pullulan | 5 | 4 | 9 | 2 | 5 | 4 |
| Polymethyl Methalacrylate | 3 | 4.5 | 7 | 4 | 3 | 3 |
| Water | QS | QS | QS | QS | QS | QS |
| Glycerin | 10 | 5 | 11 | 6 | 4 | 8 |

TABLE 3

| | Formula | | | | |
|---|---|---|---|---|---|
| Ingredient/US INCI Name | 12 % | 13 % | 14 % | 15 % | 16 % |
| Polyvalent Silicate[1] | 0.50-0.70 | 0.6-0.7 | 0.3-0.5 | 0.4-0.6 | 0.6-0.7 |
| Acrylates Copolymer | 8.0-12.0 | 6-10 | 11-15 | 2-6 | 9-13 |
| Film Former[2] | 4.0-5.0 | 3.0-4.0 | 8-10 | 2-3 | 5-4 |
| Cosmetic Powder | 3.0 | 3.0 | 3.0 | 3.0 | 3.0 |
| Water | QS | QS | QS | QS | QS |
| Plasticizer[3] | 8-10 | 4.0-6.0 | 10-12 | 5-7 | 3-5 |

[1]Vermiculite, Montmorillonite.
[2]Polyurethanes, Polysaccharides, Polyvinylpyrrolidone, Acrylates copolymer and Colloidal Silicate.
[3]Propylene Glycol, Polyethylene Glycol, Glycerol, Sorbitol, Dipropylene Glycol, Glycerin, Propanediol, Triethyl Citrate, Isohexadecane.

TABLE 4

| | Formula | | | | | |
|---|---|---|---|---|---|---|
| Ingredient/US INCI Name | 17 % | 18 % | 19 % | 20 % | 21 % | 22 % |
| Montmorillonite | 0.5 | 0.7 | 0.4 | 0.6 | 0.6 | 0.7 |
| Acrylates Copolymer | 3 | 7 | 13 | 4 | 12 | 11 |
| Pullulan | 5 | 4 | 9 | 2 | 5 | 4 |
| Polymethyl Methalacrylate | 3 | 4.5 | 7 | 4 | 3 | 3 |
| Water | QS | QS | QS | QS | QS | QS |
| Glycerin | 10 | 5 | 11 | 6 | 4 | 8 |

In making the formulations in the above tables, the following procedure may be used. The polyvalent silicate is introduced in portions with medium sweep and shear to the main kettle containing water at room temperature and mixed for about 5 to 10 minutes, or until the ingredient is fully hydrated and the mixture is homogenous. The polysaccharide is added in portions with medium sweep and shear. Then, the cosmetic powder is added. The mixture is mixed for 5 to 10 minutes or until uniform. The glycerin is added and mixed for 5 minutes or until uniform. The homogenizer is turned off. Then, the vacuum is pulled until air bubbles are removed. The anionic associative polymeric thickener is slowly added directly to the main kettle as to not cause aeration. While still under the vacuum, continue to mix the ingredients. The sodium silicate is added slowly to neutralize the thickener, using low sweep and pull vacuum. Mixing is continued until the thickener is neutralized and the formula appears uniform.

Example 2

Comparative

TABLE 5

| US INCI Name | Formula 23 % | 24 % | 25 % | 26 % | 27 % | 28 % | 29 % |
|---|---|---|---|---|---|---|---|
| Sodium Silicate | 5 | 5 | 5 | 5 | 5 | 5 | 5 |
| Polyvalent Silicate | 1 | 1 | 1 | 1 | 1 | 1 | 0 |
| Acrylates Copolymer | 3 | 3 | 3 | 3 | 3 | 3 | 3 |
| Pullulan | 5 | 5 | 5 | 5 | 5 | 5 | 5 |
| Polymethyl Methalacrylate | 3 | 0 | 0 | 0 | 3 | 3 | 6 |
| Silica | 0 | 5 | 5 | 0 | 0 | 0 | 0 |
| Sodium Hyaluronate | 0 | 0 | 0 | 0 | 0.25 | 0.5 | 0 |
| Plasticizer | 10 | 0.5 | 3.2 | 3 | 10 | 10 | 10 |
| Water | QS | QS | QS | QS | QS | QS | QS |
| TOTAL (%) | 100 | 100 | 100 | 100 | 100 | 100 | 100 |

Table 5 shows various compositions which were formed using the same process as Example 1.

If the amount of polyvalent silicate is equal to 1%, like in Formulas 23-28, the compositions (the films) crack after application to the skin. If the polyvalent silicate is not present in the formula (0%), like in Formula 29, the composition is too soft and does not provide the properties of a skin tightener. When the amount of polyvalent silicate is greater than 0% but less than 1%, or about 0.5%, the composition provides an unexpectedly strong, flexible, and durable skin tightening composition.

The present application was compared to several commercially available products such as Serious Skincare Firm-A-Face XR™ All Over Skin Tightener, Peter Thomas Roth Instant FIRMx Temporary Face Tightener, Fusion Beauty Nip Line Erase Instant Line Remover, Hydroxatone 90 Second Wrinkle Reducer, NuNutrients Facelift, Renoir No Lines Temporary Wrinkle Remover and Instantly Ageless®. The commercially available products provided a tightening sensation and visual changes to the skin within 5 minutes. Nonetheless, they also presented many negative characteristics upon drying such as whitening, cracking of the film, and incompatibility with the various makeup regiments. Furthermore, the beneficial results (e.g., the skin tightening properties) were not long-lasting. The compositions of the instant disclosure were long-lasting. The compositions retained their beneficial results (e.g., the skin tightening properties) without whitening, cracking, or peelings for a much longer period of time than the commercially available products, e.g., longer than 30 min, 1 hour, 3 hours, 4 hours, 5 hours, or 6 hours.

In the section below, Formula 6 from Example 1 (Table 2) is compared with Instantly Ageless®. Instantly Ageless® contains sodium silicate, magnesium aluminum silicate, acetyl hexapeptide-3, phenoxyethanol, ethylhexylglycerin, water, Yellow 5 and Red 40.

To compare the two compositions, an instrumental evaluation, utilizing the Cutometer MPR 580 (Courage and Khazaja, Köln, Germany), was carried out. The Cutometer Study measures the skin elasticity of the eyebags. The objective of this study is to collect cutometer data to determine the relationship between skin elasticity and aesthetician grading for eyebag appearance and to correlate changes in skin elasticity and wrinkle visibility after application of film technology with changes in eyebag grade.

An expert evaluation of eye bags was also performed by an aesthetician using a 7 point scale atlas grading. The efficacy of the product was examined at T=0, 10 min, 30 min, 3 hours, and 6 hours. Women with baseline Grade 4 eye bags experience an average of 2.5 grade reduction in puffiness for 6+ hours after application of the compositions described herein.

After application of Instantly Ageless® to the skin, an immediate tightening of the skin was observed, but the tightening almost immediately began to dissipate and the product formed white film, cracked, and caused slight irritation. Instantly Ageless showed an average reduction of 1 grade with a higher tendency of film flaws such as whitening and cracking. On the contrary, the inventive compositions exhibited long-lasting results for at least 6 hours and an average of 2.5 grade reduction in eye bag puffiness.

Figure 2:
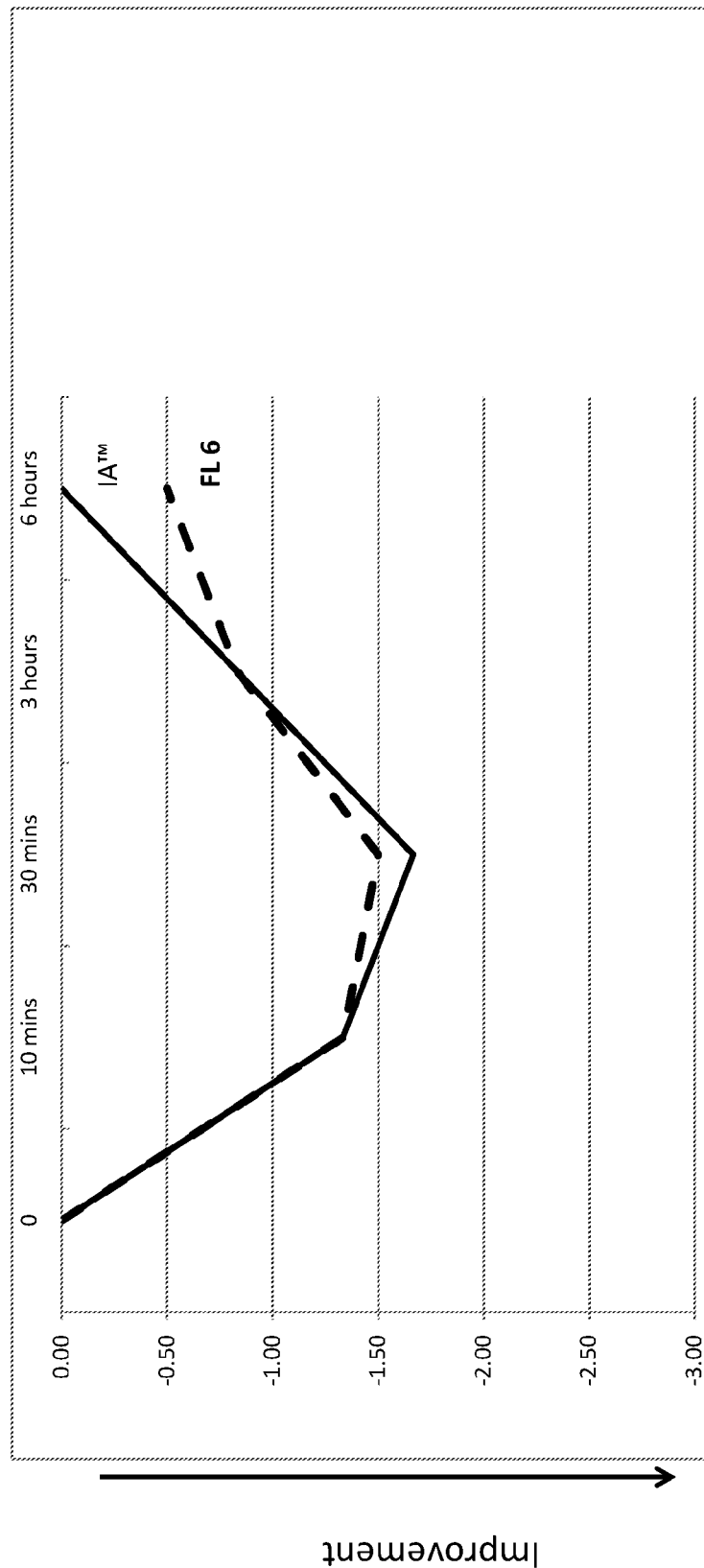
FIG. 2 is a graph comparing the results of inventive Formula 6 and the commercially available product Instant Ageless® on crow's feet. The graph illustrates time versus improvement of crow's feet.

FIGS. 1 and 2 compare the inventive example and the commercially available product Instantly Ageless®. FIG. 1 represents the reduction of under eye bags over time. The study was completed with 6 Caucasian women aged 40-60 years with Grade 4 eye bags (Aging Atlas grade).

As observed in FIG. 1, the inventive composition provided dramatic results compared to Instantly Ageless®. An instant improvement was noticeable in 10 minutes and lasted over 6 hours. On the other hand, whitening, flaking, and cracking, appeared within only 3 hours with Instantly Ageless®.

FIG. 2 represents the reduction of crow's feet. The inventive composition provided longer lasting results compare to Instantly Ageless®. The inventive composition showed only very slight film flaws after 3 hours; whereas film flaws began appearing at 30 minutes for Instantly Ageless®.

Example 3

Film Property Tests

Thickeners were tested according to three criteria: compatibility, viscosity, and tightening. Below is a Table of the different thickeners tested with their results.

TABLE 6

| Thickeners | | | |
|---|---|---|---|
| INCI Name | Compatibility | Viscosity | Tightening |
| Acrylates/steareth-20 methacrylate copolymer[1] | + | − | + |
| Acrylates/beneneth-25 methacrylate copolymer[2] | + | + | + |
| PVP[3] | − | + | + |
| Acrylates/C10-30 alkyl acrylate copolymer[4] | − | − | N/A |
| Acrylates/beneneth-25 methacrylate copolymer[5] | + | − | + |
| Acrylates/steareth-20 methacrylate copolymer[6] | + | − | + |
| Acrylates/C10-30 alkyl acrylate copolymer[7] | − | − | + |
| Acrylates/C10-30 alkyl acrylate copolymer[8] | − | − | + |
| Acrylate copolymer[9] | + | + | + |
| Acrylates/C10-30 alkyl acrylate copolymer[10] | + | + | − |

TABLE 6-continued

Thickeners

| INCI Name | Compatibility | Viscosity | Tightening |
|---|---|---|---|
| Acrylates/C10-30 alkyl acrylate copolymer[11] | + | − | − |
| Montmorillonite[12] | + | + | + |

[1]Aculyn 22 Polymer, available from Dow Chemical.
[2]Novethix L-10 Polymer, available from Lubrizol.
[3]Flexithix, available from Ashland
[4]Carbopol 1382 Polymer, available from Lubrizol.
[5]Aculyn 28 Polymer, available from Lubrizol.
[6]Aculyn 88 Polymer, available from Lubrizol.
[7]Carbopol Ultrez 21 Polymer, available from Lubrizol.
[8]Carbopol Ultrez 20 Polymer, available from Lubrizol.
[9]Carbopol Aqua SF-1 Polymer, available from Lubrizol.
[10]Pemulen TR-2 Polymer, available from Lubrizol.
[11]Pemulen TR-1 Polymer, available from Lubrizol.
[12]GelWhite-H XR, available from BYK Additives & Instruments.

Table 6 shows that the acrylates/beneneth-25 methacrylate copolymer, the acrylates copolymer, and the montmorillonite presented positive results (+) for all three parameters: compatibility, viscosity and tightening.

Film formers were tested according to three criteria: compatibility, formed film, and tightening. Below is a table of the different film formers tested with their respective results.

TABLE 7

Film Formers

| INCI Name | Compatibility | Formed Film | Tightening |
|---|---|---|---|
| Polyurethane-35[1] | + | − | − |
| Polyurethan-2 (and) Polymethyl methacrylate[2] | + | − | − |
| Pullulan | + | + | + |
| PVP[3] | + | + | − |
| Polycacrylate-21 (and) acrylates/dimethylaminoethylmethacrylate copolymer[4] | + | + | + |
| Polyacrylate-2 crosspolymer[5] | − | N/A | N/A |
| Polyacrylate-32[6] | + | − | − |
| AMP-acrylates/allyl methacrylate coloymer[7] | + | − | − |
| Silica[8] | + | + | + |
| Sodium Silicate | + | + | + |

[1]Baycusan C 1004, available from Bayer Material Science.
[2]Hybridur 875 Poymer Dispersion, available from Air Products.
[3]PVP K30L, available from Ashland.
[4]Syntran PC5100 CG, available from Interpolymer
[5]Fixate Superhold Polymer, available from Lubrizol
[6]Fixate Design Polymer, available from Lubrizol
[7]Fixate G100L PR Polymer, available from Lubrizol
[8]Colloidal Silica, Ludox AM X6021, available from Grace Davison.

Pullulan, polycacrylate-21 (and) acrylates/dimethylaminoethylmethacrylate copolymer, silica, and sodium silicate provided the best film-forming properties, as shown by the positive (+) results for all three properties: compatibility, formed film, and tightening.

A standard safety test for eye products, called BCOP (Bovine Corneal Opacity and Permeability), was conducted in vitro to measure the level of irritation of the products. The results showed that the inventive composition was cosmetically acceptable and caused only mild, if any, irritation.

Example 4 pH Study with Composition Containing Sodium Silicate

A study of the pH was performed. The results showed that if the pH is below 10, the composition became more solid. However, it was found that when the pH is in the range of 10 to 12, or 11 to 11.5, the composition exhibits special properties. For example, the composition exhibited excellent film-forming properties on the skin and the film exhibited unexpectedly long-lasting strength, durability, and flexibility (elasticity).

As used herein, all percentages are by weight (wt. %) of the total composition.

All numeric ranges are inclusive of narrower ranges; delineated upper and lower range limits are interchangeable to create further ranges not explicitly delineated. All ranges and values disclosed herein are inclusive and combinable. For examples, any value or point described herein that falls within a range described herein can serve as a minimum or maximum value to derive a sub-range, etc.

As used herein, the term "tightening" means that the film contracts in a manner that skin has a tighter sensation to the user, and smoothes skin imperfections upon application on the skin, which reduces the visual appearance of wrinkles in the skin.

As used herein, the terms "comprising," "having," and "including" are used in their open, non-limiting sense.

The terms "a," "an," and "the" are understood to encompass the plural as well as the singular.

The expression "at least one" means "one or more" (and vice versa) and thus includes individual components as well as mixtures/combinations.

"Film former" or "film forming agent" as used herein means a polymer or resin that leaves a film on the substrate to which it is applied, for example, after a solvent accompanying the film former has evaporated, absorbed into and/or dissipated on the substrate.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The foregoing description illustrates and describes the disclosure. Additionally, the disclosure shows and describes only the exemplary embodiments but, as mentioned above, it is to be understood that it is capable to use in various other combinations, modifications, and environments and is capable of changes or modifications within the scope of the disclosed concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

The invention claimed is:

1. A skin tightening aqueous film forming composition comprising:
   (a) 5% to 10% by weight of sodium silicate and 1% to 10% by weight of pullulan;
   (b) 0.3% to 0.7% by weight of montmorillonite, bentonite, or a mixture thereof;
   (c) 1% to 13% by weight of acrylates copolymer;
   (d) 2% to 15% by weight of at least one plasticizer selected from the group consisting of glycerin, propylene glycol, butylene glycol, and propanediol; and
   (e) 1% to 8% by weight of polymethyl methacrylate powder;
   wherein the composition provides a tightening sensation and smoothes skin imperfections upon application to the skin.

2. The composition of claim 1 comprising montmorillonite.

3. A method for improving the appearance of skin, firming the skin, and/or tightening the skin comprising applying the composition of claim 1 to the skin.

* * * * *